United States Patent [19]

Failla et al.

[11] Patent Number: 4,741,336
[45] Date of Patent: May 3, 1988

[54] SHAPED STAPLES AND SLOTTED RECEIVERS (CASE VII)

[75] Inventors: Stephen J. Failla, Chester; Carmen Gerrone, Stockton, both of N.J.

[73] Assignee: Ethicon, Inc., Somerville, N.J.

[21] Appl. No.: 838,869

[22] Filed: Mar. 12, 1986

Related U.S. Application Data

[63] Continuation-in-part of Ser. No. 631,115, Jul. 16, 1984, abandoned.

[51] Int. Cl.$^4$ ............ A61B 17/08; F16B 15/00; B31B 1/00
[52] U.S. Cl. .................. 128/334 R; 128/334 C; 227/19; 411/457
[58] Field of Search ............... 128/334 R, 334 C, 335; 411/457, 511, 512, 518, 908, 920, 475; 227/19, DIG. 1, 135; 24/572, 583, 58, 84, 85, 587

[56] References Cited

U.S. PATENT DOCUMENTS

| | | | |
|---|---|---|---|
| 506,861 | 10/1893 | Prentice | 411/475 |
| 3,757,629 | 9/1973 | Schneider | 411/920 |
| 4,014,492 | 3/1977 | Rothfuss | 227/19 |
| 4,403,693 | 9/1983 | Froelich | 411/457 |
| 4,505,273 | 3/1985 | Braun et al. | 128/334 R |
| 4,506,670 | 3/1985 | Crossley | 128/334 C |
| 4,506,671 | 3/1985 | Green | 128/334 C |
| 4,513,746 | 4/1985 | Aranyi et al. | 128/334 C |
| 4,534,350 | 8/1985 | Golden et al. | 128/334 C |
| 4,548,202 | 10/1985 | Duncan | 128/334 C |
| 4,573,469 | 3/1986 | Golden et al. | 128/334 C |
| 4,602,634 | 7/1986 | Barkley | 128/334 C |
| 4,610,250 | 9/1986 | Green | 128/334 C |

FOREIGN PATENT DOCUMENTS

| | | | |
|---|---|---|---|
| 8501430 | 4/1985 | European Pat. Off. | 128/334 C |
| 2016 | 1/1906 | United Kingdom | 411/457 |

*Primary Examiner*—Richard C. Pinkham
*Assistant Examiner*—Gary Jackson
*Attorney, Agent, or Firm*—Robert L. Minier

[57] ABSTRACT

A surgical instrument for joining tissue by means of a two piece fastener. The fastener is a shaped staple having a general shape of an M, and a receiver for engaging with the legs of the staple. The staple has an M-shape with the outer legs portions being non-parallel or parallel. The legs of the staple are connected by a compressibly resilient portion. The staple legs penetrate the tissue and engage and interlock with the openings in the receiver.

10 Claims, 7 Drawing Sheets

SHAPED STAPLES AND SLOTTED RECEIVERS (CASE VII)

This is a continuation-in-part application of copending patent application Ser. No. 631,115 filed July 16, 1984 and since abandoned.

This invention relates to fasteners for use in joining human or animal tissue and to instruments for use with such fasteners. One part of the fastener is a M-shaped staple and the other part of the fastener is a receiver which interlocks with the legs of the staple to form the fastener.

BACKGROUND OF THE INVENTION

Over the years various surgical instruments for joining tissue have been developed. Most instruments have been developed utilizing metal staples for joining the tissue. The metal staples are relatively rigid, have their legs sharpened to readily penetrate the tissue, and once penetrated may then be crimped into a clinched position to hold the tissue together as is well known in the art. Instruments of this type are more fully disclosed and described in U.S. Pat. Nos. 3,080,564, 3,079,606, 2,891,250, 3,589,589, 4,207,898 and 4,351,466.

Generally, the instruments comprise a movable member or jaw and a stationary member or jaw. The movable jaw usually carries the metal staples and the stationary jaw carries an anvil which clinches or bends the legs of the staple that pass through the tissue. In use, the tissue is placed between the jaws, the jaws brought to the appropriate gap and the staples driven through the tissue and clinched to set the staple. A major problem with these instruments is the use of the metal staple. While metal staples provide desired hemostatsis in the joining of the tissue, they remain in the tissue and can disrupt future diagnostic techniques such as x-ray diagnosis, computer axial tomography, nuclear magnetic resonance, and the like. To eliminate this problem, it has been found desirable to develop instruments which can set non-metallic fasteners. These are fasteners made from biologically absorbable or non-absorbable polymeric materials. Examples of the absorbable polymeric materials would be the polymers and copolymers of glycolide, lactide, dioxanone, etc. These polymeric materials do not have the dead-bend morphology of a metal and, hence, they cannot be clinched in the same manner as a metal staple. To use these polymers, the fasteners are designed as two-piece fasteners. This means one piece of the fastener is placed on one side of the tissue to be joined and the second piece of the fastener is placed on the other side of the tissue to be joined. One piece of the fastener is a U-shaped staple which has legs which are caused to penetrate the tissue. On the opposite side of the tissue is the second fastener piece or receiver which is a member used to engage the legs to interlock therewith once the legs have penetrated the tissue and, hence, join the tissue together.

As can be appreciated this major change in design and configuration of fasteners causes a number of problems. First, the fasteners must be designed to be sufficiently sharp and strong to penetrate the tissue or in certain instances some arching means must be used with the fastener to assist in penetrating the tissue. Also, the fasteners must be designed to develop an interlocking between the two pieces.

When applying these fasteners the instrument must hold the pieces until one piece has penetrated the tissue and the opposite piece is interengaged and locked on to the penetrating portion of the other member. Once this is accomplished the instrument must then release both pieces preferably simultaneously.

The instrument must be designed to firmly hold both pieces of the fasteners until the instrument is correctly positioned and the fasteners ready to be placed to join the tissue. The instrument must then uniformly and smoothly release both pieces of the fasteners as the tissue is joined. All instruments should perform these functions in an identical manner so that surgical techniques are uniform and the surgeons can rely on the instrument performing in the same manner each time they are used. Also, in view of today's emphasis on medical costs, the instrument should be economical to produce.

It is an object of the present invention to provide fasteners which are reliably held by an instrument and simply and reliably released by the instrument at an appropriate time. It is a further object of the present invention to provide a two-piece fastener that reliably aligns itself and interlocks when joining tissue. It is yet another object of the present invention to provide fasteners and instruments that are simple in construction and economical to produce.

SUMMARY OF THE PRESENT INVENTION

The present invention provides two-piece fasteners for joining tissue. The fasteners comprise a shaped staple member with the staple having the general shape of an M, and a receiver for engaging with the legs of said staple member. The fasteners are applied using a surgical instrument and the instrument places the staple member on one side of the tissue to be joined and the receiver on the opposite side of the tissue. The instrument causes the staple legs to penetrate the tissue and engage and interlock with the receiver or it may merely crimp the staple legs when no receiver is used. The instrument comprises a support body. Mounted at one end of the support body is a pair of jaws. A staple housing is mounted in one of the jaws and this jaw is movable with respect to the other of said jaws. Means are mounted in the support body for moving the jaw housing the staples towards the stationary jaw to close the gap between the jaws and clasp the tissue therebetween. Drive means are mounted on the support body for driving the staples from the jaw in which the staple housing is mounted towards the opposite jaw. Actuating means are mounted at the end of the support body opposite the end at which the jaws are mounted for actuating the staple drive means. Cooperating with the open end of the jaws is a means to hold tissue in place between the jaws while the staples are being driven.

The staple portion has an M shape with the outer leg portions parallel or non-parallel. The legs of the staple are connected by a compressibly resilient portion. The staples are frictionally held in the jaw of the instrument by squeezing the outer legs of the staple together. The receiver includes a pair of openings for engaging the legs of the staple together. The receiver includes a pair of openings for engaging the legs of the staple after the legs of the staple have punctured the tissue to be joined to interlock therewith. Such interlocking may be caused by a friction or interference fit or by similar locking means. In one embodiment of the receiver of the present invention, the openings in the receiver, on the side of the receiver facing the staple, are considerably larger in diameter than the diameter of the staple legs they have to accept and the openings are tapered to a smaller than the diameter of the staple legs, to form a tight fit therewith. In another instrument of the present invention, the openings in the receiver are oval or elliptical in shape with the longer directions of the ovals being positioned to accept the spreading of the M-shaped staple to provide for ready alignment of the legs of the staple with the openings in the receiver. Other fasteners and details of the present invention will be discussed in the ensuing detailed description and drawings.

DETAILED DESCRIPTION OF THE DRAWINGS

Figure 1:
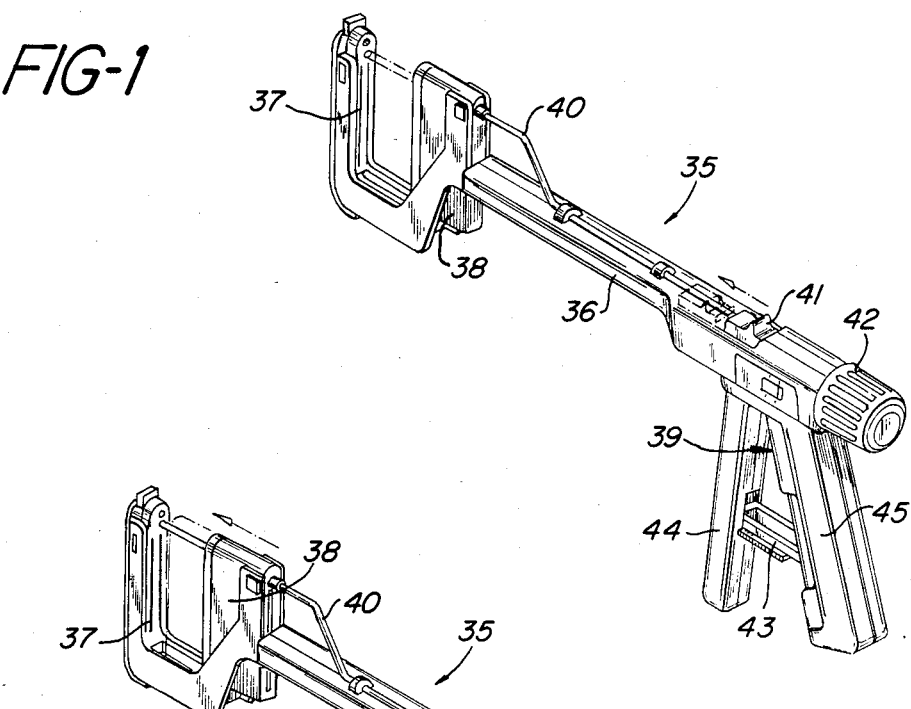
FIG. 1 is a perspective view of an instrument according to the present invention in its fully opened position.
Figure 2:
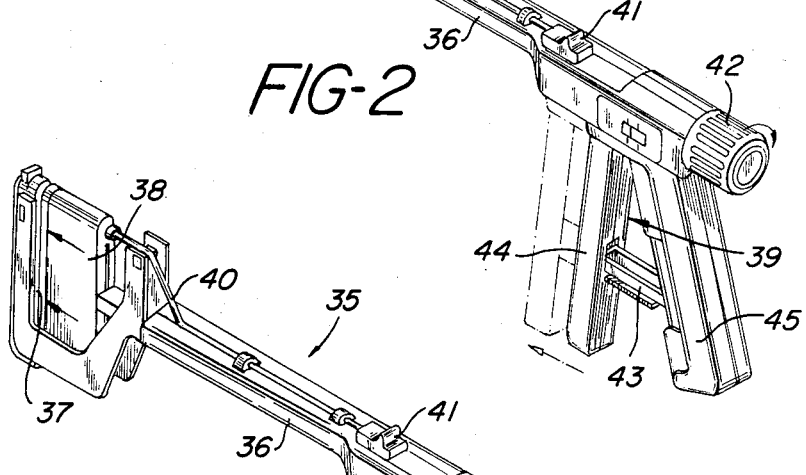
FIG. 2 is a perspective view of the instrument of FIG. 1 in a partially open position.
Figure 3:
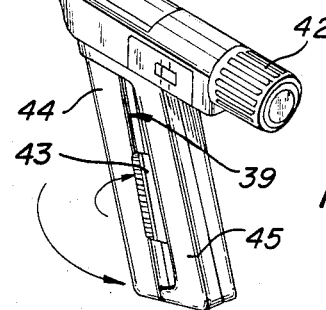
FIG. 3 is a perspective view of the instrument of FIG. 1 in its firing position.

Referring to the drawings, in FIGS. 1, 2, and 3 there is depicted a surgical instrument 35 of the present invention useful for joining tissue. The instrument is depicted in three different positions.

In FIG. 1, the instrument is shown in the fully open position. The instrument comprises a support body, 36. A pair of jaws 37 and 38 are positioned at one end of the support body. Mounted at the opposite end of the support body is means 39 for actuating the instrument. In FIG. 1, the jaws of the instrument are in the open position ready to be placed about the tissue to be joined.

In FIG. 2, the jaws have been moved closer to one another to produce an appropriate gap to clamp tissue in position between the jaws so that the tissue is ready to be stitched together.

FIG. 3 shows the instrument after it has been actuated and the tissue has been joined by the instrument.

One of the jaws 37 is stationarily mounted at one end of the support body 36. This jaw carries a plurality of receivers of the two-part fastening members used with the instruments of the present invention. The opposite jaw 38, carries the W-shaped fastening members, and is movably mounted on the support body. The tissue to be joined is placed between the two jaws and the movable jaw positioned with respect to the stationary jaw at an appropriate gap. Once the tissue is placed between the jaws, the locking arm 40 is moved forwardly by the pusher 41 to insure that the tissue is held between the jaws. Once the arm is set and engaged by the stationary jaw, the knob 42 at the opposite end of the support body is turned to move the movable jaw towards the stationary jaw and set the appropriate gap between the jaws. Once the gap has been appropriately set, the trigger locking lever 43 may be disengaged and the movable portion 44 of the actuating trigger means moved towards the stationary portion 45 of the trigger means to cause an appropriate pusher to drive the staples forward causing the legs of the staples to penetrate the tissue between the jaws and the legs of the staples to enter the appropriate receivers held in the stationary jaw. Once this is accomplished the knob 42 may be turned in the opposite direction to open the jaws, the locking lever pushed back and the joined tissue separated from the jaws of the instrument.

Figure 4:
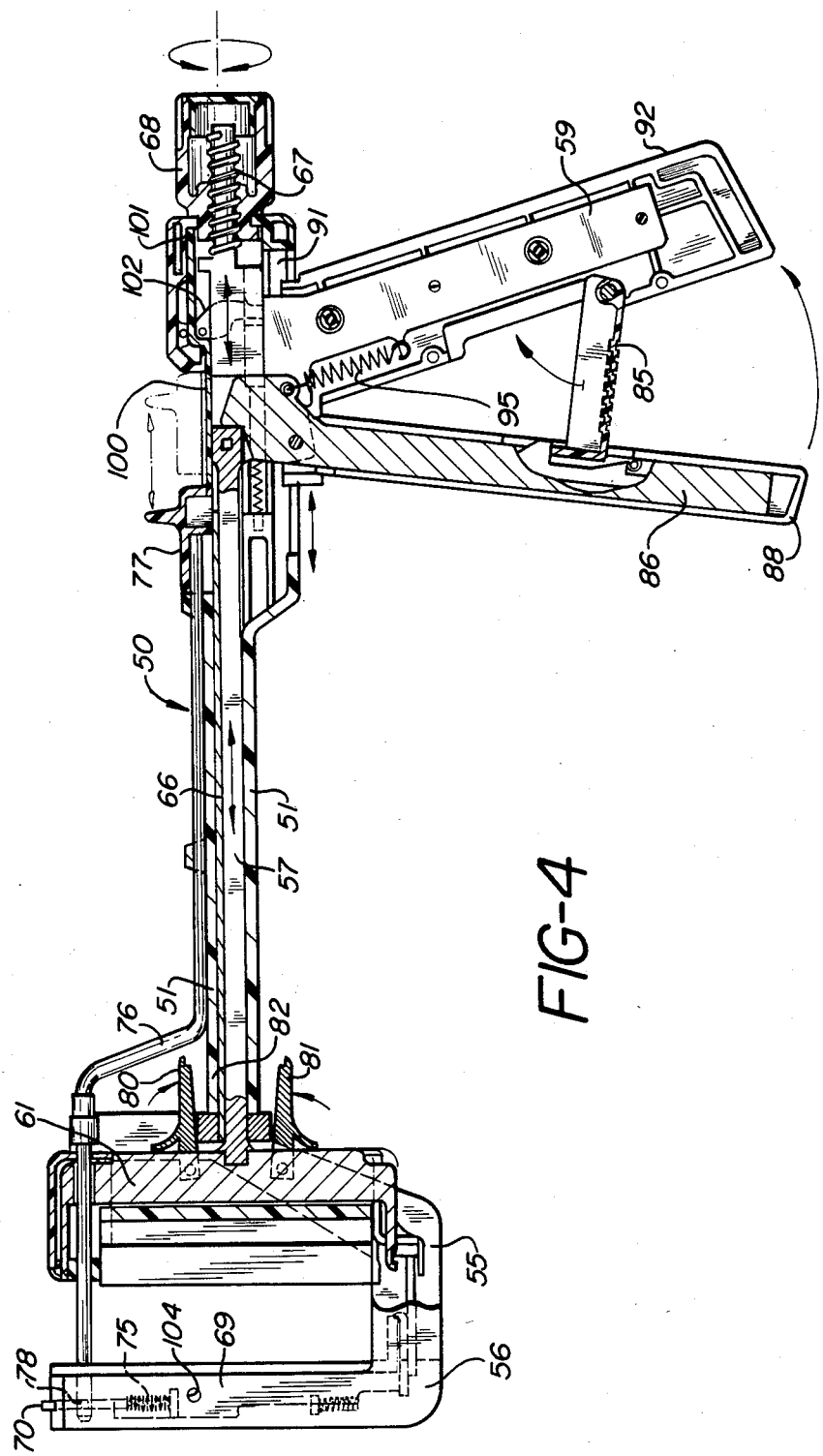
FIG. 4 is a cross-sectional view of another embodiment of a surgical instrument according to the present invention.
Figure 5:
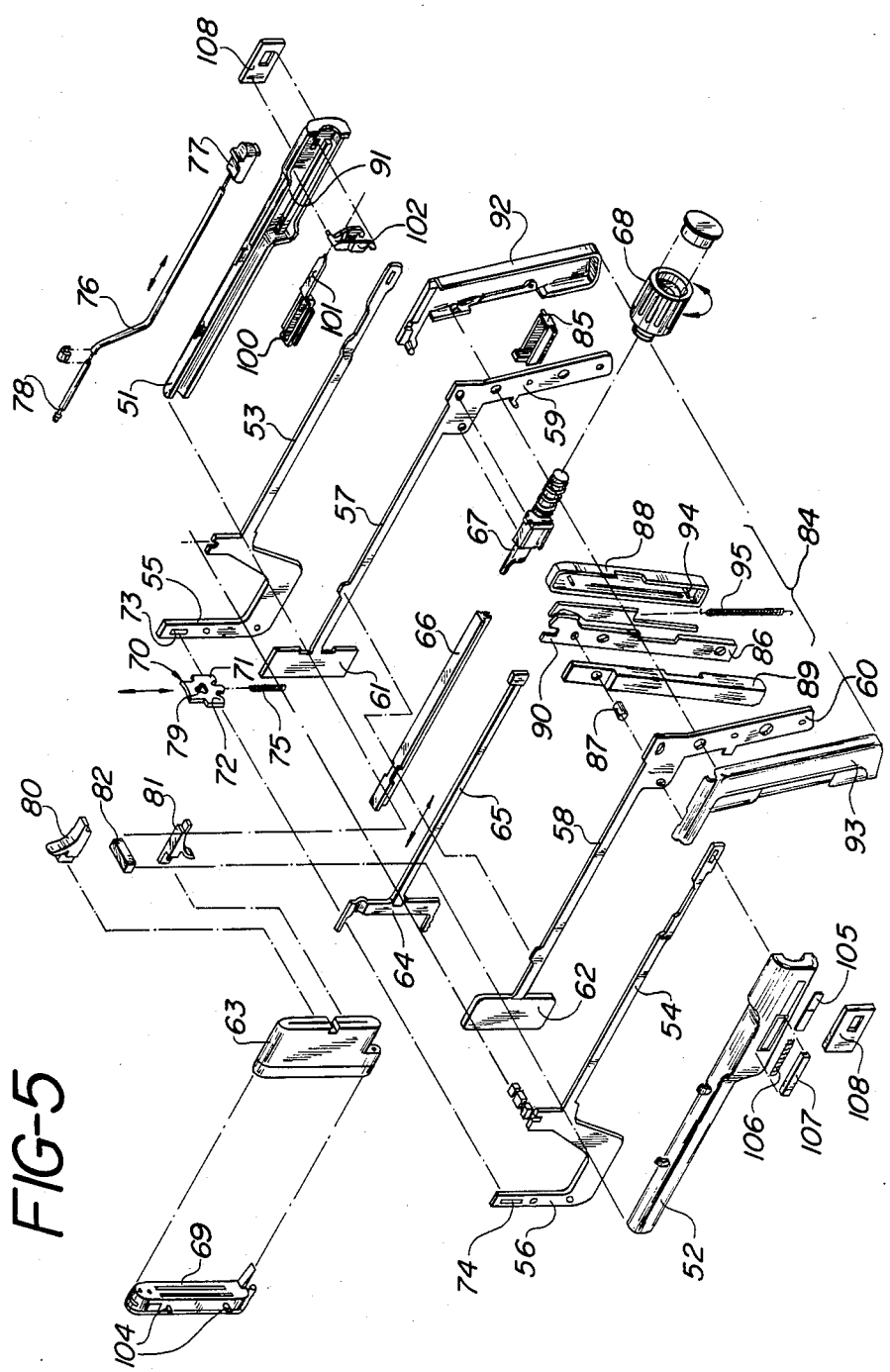
FIG. 5 is a exploded perspective view of the surgical instrument of FIG. 4.

FIG. 4 is a cross-sectional view of one embodiment of a surgical instrument according to the present invention and FIG. 5 is an exploded perspective view showing the different parts of the surgical instrument shown in FIG. 4. The body 50 of the instrument comprises a pair of outer cover members 51 and 52 which when pressed together form a hollow opening longitudinally disposed therebetween. Mounted in this opening are a pair of shafts 53 and 54 which, at one end, carry stationary supports 55 and 56 which together form the stationary jaw. The jaw is held together by riveted pins 104 located in holder 69. Also carried in the opening is a second pair of shafts 57 and 58 which carry at one end the supports 59 and 60 for the stationary portion of the actuating means and at the opposite end carry the supports 61 and 62 for the movable jaw. A holder 69 for the receiver portions of the fasteners is mounted between the stationary jaw supports and the holder 63 for the M-shaped staple portion of the fasteners is mounted between the movable jaw supports 61 and 62. A pusher 64 is mounted on a shaft 65 disposed in the center of the opening formed by the outer cover members. Mounted on top of the center shaft 65 is a movable member 66. The movable member is appropriately mounted through a screw 67 to the knob 68. Turning of the knob in one direction moves the pusher and the staple holder forwardly towards the receiver holder to set an appropriate gap between the staples and the receivers. Turning the knob in the opposite direction moves the pusher and staple holder away from the receiver holder to open the gap and allow tissue to be removed from between the staple holder and receiver holders. Mounted between the supporting jaw members at the top thereof is a portion of means for holding tissue between the jaws and for locking the top of the jaws together to provide rigidity. This portion comprises a movable slotted member 70 having a pair of ears 71 and 72. The ears are disposed in slots 73 and 74 disposed in stationary supports 55 and 56. A compression spring 75 is mounted beneath the slotted member to allow the member to move up and down in the slots disposed in the stationary jaw members. Mounted on top of the outer cover members 51 and 52 and longitudinally thereto is the cooperating portion of the means for holding tissue and locking the jaws together for rigidity. This cooperating portion is a longitudinal movable member 76 that fits through an opening in the upper portion staple holder member 63. The longitudinally movable member is movable forwards and backwards with respect to the outer cover and is moved by the thumbs press 77. The movable member has a slot 78 at its free end and when moved forwardly, interlocks with the opening 78 in the movable slot member 70. A dog depends from the thumb press 77 and fits into grooved member 100 mounted at the back and on top of the cover members. At the opposite end of the groove is a portion 101 that extends inwardly and engages in a slot in the knob 68. The portion 101 is guided in its movement by outer covers 51 and 52. Until the member is pushed as far forwardly as possible to remove the portion 101 from the slot in the knob, the knob cannot be rotated. Mounted from the staple holder are a pair of pawls 80 and 81 and mounted on the rigid shifts 53 and 54 is an anchor 82. The pawls are so disposed as to interlock with the anchor when the appropriate gap is set between the staple holding member 63 and the receiving holding member 69. The interlocking pawls and anchor provide added rigidity to the instrument and allow greater forces to be used when driving the staples through the tissue and into locking relationship with the receivers. At the opposite end of the instrument is mounted the trigger or actuating means 84. The actuating means comprises a movable trigger portion mounted between the supports 57 and 58 by a pin 87. A pivotal member 86 is encased by interlocking plastic handle halves 88 and 89 of the movable trigger portion. The pivotal member includes an ear 90 which engages the shaft 65. The actuating means 84, member 61 and 62 and the shaft 65 are slideably mounted in slot 90 in the outer cover members 51 and 52. The stationary trigger portion comprises a pair of plastic handle halves 92 and 93. Mounted between the movable trigger portion and the stationary trigger portion is a pivotal interlocking member 85. This member is pivotally mounted between the stationary handles 92 and 93 and interlocks by engaging a pin 94 spring mounted 95 in the movable portion of the trigger member. Mounted in the cover member 52 is a gauge to tell when the correct gap is attained between the receiver holder and the staple holder. The gauge comprises a marked member 105 that is linked to the screw member 67 and is mounted in position on the cover member 52 by a spring 106 and cover plate 107. Appropriate cover plates 108 for identification and to see the mark on the marked member are placed on the outside of the cover members.

Figure 6:
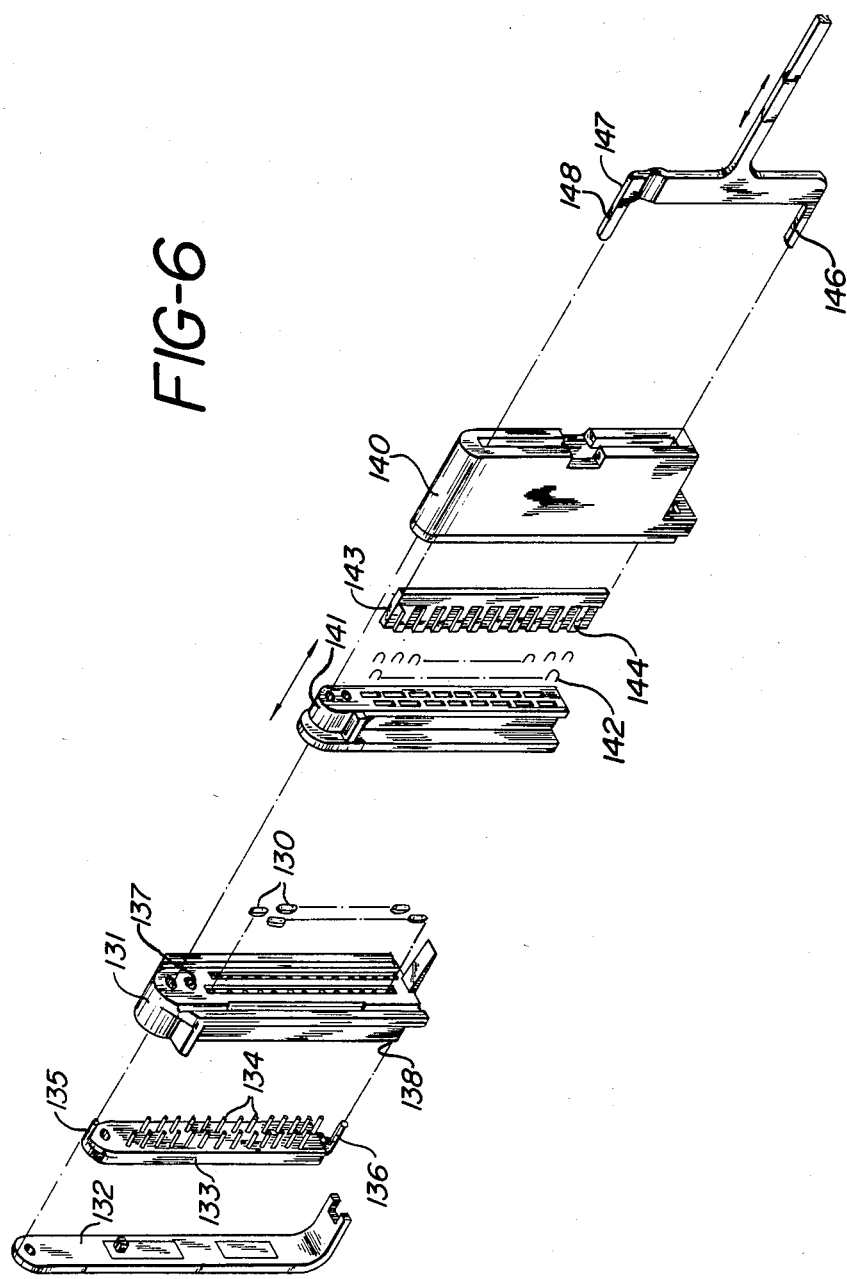
FIG. 6 is an exploded perspective view of the working parts of one embodiment of the jaws of an instrument of the present invention.

Referring to FIG. 6 there is shown an exploded perspective view of one embodiment of the working parts of the pair of jaws of instruments according to the present invention. Receivers, and in this instance they comprise members having a pair of openings disposed therein, are mounted in a stationary jaw and M-shaped staples with the legs of the M designed to enter the openings of the receivers are mounted in the movable jaw. The receivers 130 are mounted in a housing 131 mounted on the stationary jaw 132. The receivers are held in that housing by a movable member 133 which has pins 134 which frictionally engage the openings in the receivers. This holding member is movably mounted by virtue of an upper and a lower pin 135 and 136 respectively positioned in openings 137 and 138 in the receiver housing 131. The movable jaw 140 carries a housing 141 for holding the M-shaped staples 142. Mounted behind this housing is a first pusher means 143 having fingers 144 which engage the back end or the span of the M-shaped staples. Second drive means 147 mounted at the rear of the jaw moves forwardly to drive the first drive means and push the staples out of the housing so that the legs of the staples engage the receiver. Along therewith pins 146 and 148 of the second drive means engage the pins 135 and 136 and push the pins through the opening in the housing into the receiving housing opening to push the pins 135 and 136 out of frictional engagement with the receivers thus allowing the receivers to interlock with the legs of the staple.

Figure 7:
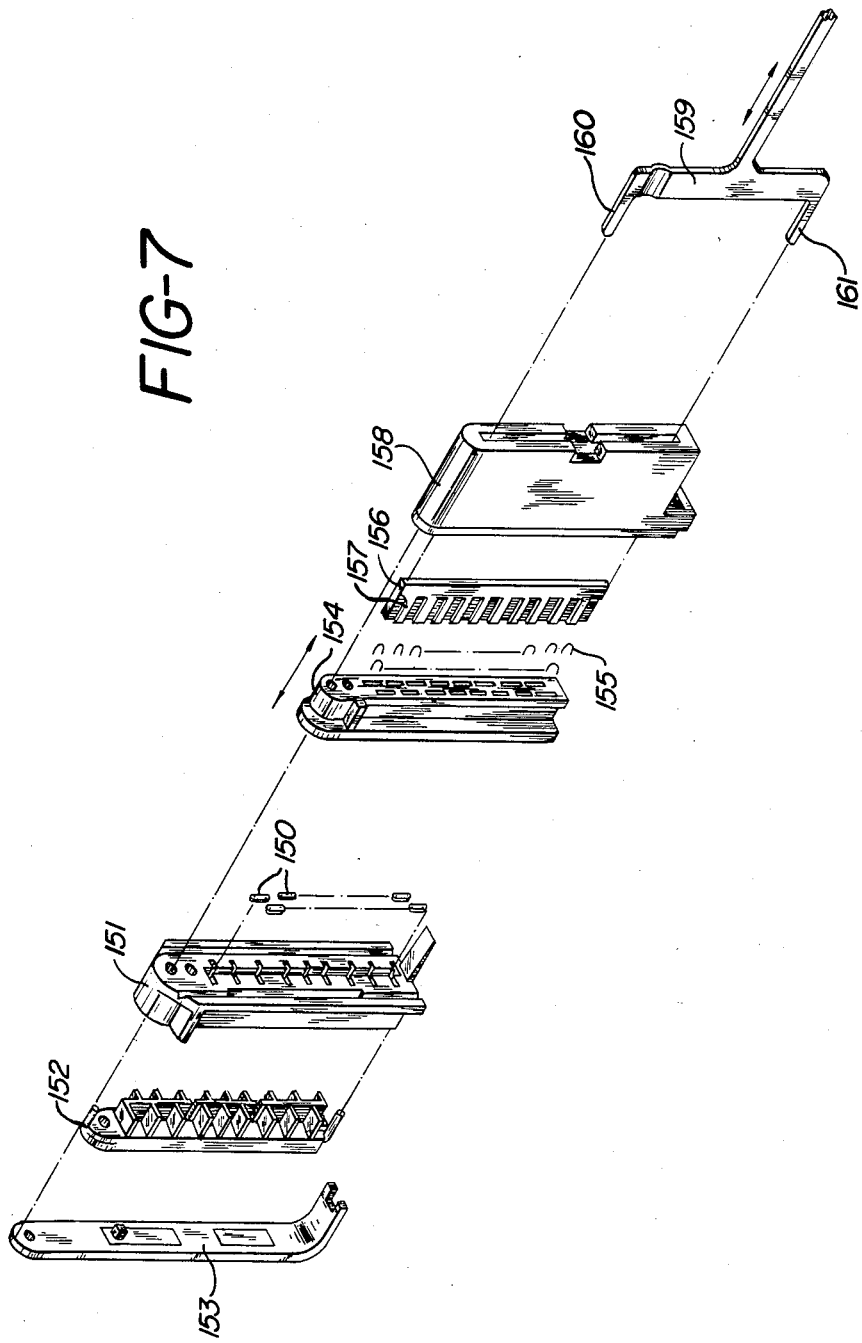
FIG. 7 is an exploded perspective view of the working parts of another embodiment of the jaws of an instrument of the present invention.

In FIG. 7 there is an exploded perspective view of another embodiment of the stationary and movable portions of the jaws for holding two-piece staples. In this embodiment the receivers 150 are held in a housing member 151 by a movable friction holding member 152 disposed within the housing. This friction member engages the outer periphery of the receivers to frictionally hold them within the housing. The receiver holding member and the friction holding member are mounted on the stationary jaw 153. A movable jaw 158 similar to that depicted in FIG. 6 comprises a staple housing member 154 for holding M-shaped staples 155. A first drive means 156 comprising individual fingers 157 which engage the staples to drive them. A second drive means 159 fits within the jaw to drive the first drive means and to also drive pins 160 and 161 at the same time that it drives the staple to cause the receiver friction holding member to move backward and disengage from the receivers allowing the receivers to be interlocked with the M-shaped staples.

An important part of the instruments of the present invention are the means for releasable holding individual staples in a manner to allow them to be appropriately driven through tissue to be joined and to have the legs of the staple align themselves in the openings of the receiver to interlock therewith.

Figure 8:
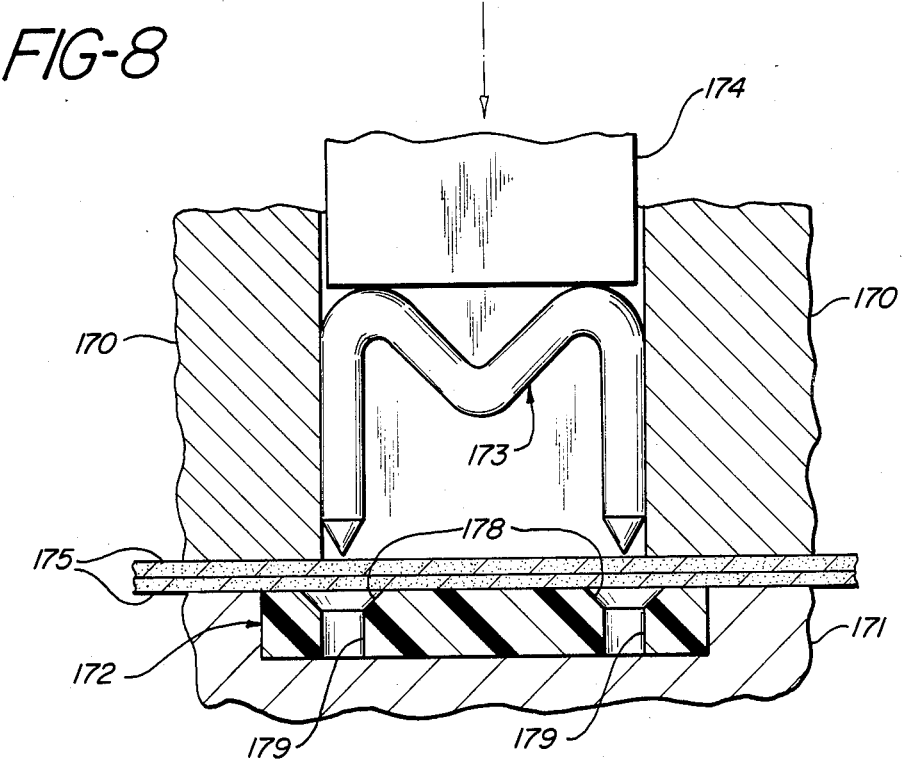
FIG. 8 is an enlarged cross-sectional view of a staple and receiver in the jaws of an instrument of the present invention.
Figure 9:
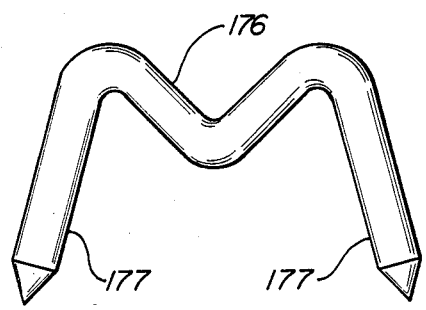
FIG. 9 is an enlarged view of a staple of the present invention.

As more clearly shown in FIGS. 8 and 9, the M-shaped staples are held in the instrument by virtue of the configuration of the staple. FIG. 8 is an enlarged cross-sectional view of the staple holding portion of a movable jaw 170 and the receiver holding portion of a stationary jaw 171 showing a receiver 172 according to the present invention in place in the stationary jaw. A staple 173 according to the present invention is in place in the movable jaw and the individual finger 174 driving means for driving the staple is shown. The positioning of the jaws has been somewhat moved apart for the sake of clarity. In actual use, the tissue 175 is not rigid but is rather conformable and would tend to fill up the entire gap between the jaws. The staple is held in position in the jaw by the frictional engagement caused by the legs of the staple pressing against the jaw. As more clearly shown in FIG. 9, in a preferred embodiment of the staple 176 of the present invention the legs 177 of the staple are not parallel but diverge from each other. The staple is held in the instrument by bringing the legs towards each other and having the jaws of the instrument maintain the legs substantially parallel. As can be appreciated, by urging the legs towards each other in order to hold the staple in the instrument when the staple is released from the instrument, the legs will tend to diverge. This divergence may cause the staple leg to be misaligned with its interlocking openings in the receiver. One way of insuring that the leg will meet the receiver opening is shown in FIG. 8. The side of the receiver opening facing the staple has a tapered portion 178. This portion has an initial diameter larger than the diameter of the staple leg to interlock therewith.

Figure 12:
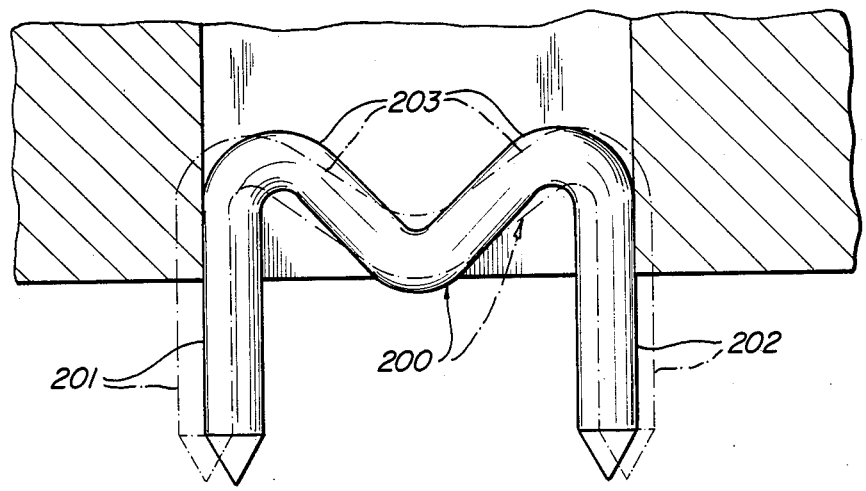
FIG. 12 is an enlarged cross-sectional view of a staple of the present invention in the staple holding portion of an instrument.

An alternate method of retaining the staples in the staple holding portion of the movable jaw is shown in FIG. 12. In this embodiment, the staple 200 is made with parallel legs 210 and 202 that are wider than the staple holding slot as shown in phantom. When inserted into the slot the staple is forced to distort to a smaller width (solid lines) to conform to the slot. The M-shaped crown 203 is capable of sustaining this distortion by closing together in an accordion-like manner. The advantage of this embodiment is that the legs will remain parallel as they exit from the slot and approach the receiver holes.

In all embodiments of the staples of the present invention the staples are made from a single piece of polymeric material with the connecting portion of the staple; i.e. the portion connecting the two legs, being compressibly. This property of compressive resiliency combined with the M-shape configuration of the staple allows the staple to be held in an instrument by urging the staple leg towards one another. By so compressing the legs, the single piece polymeric construction urges the legs against the opening in the instrument to hold the staples in the instrument until they are discharged. Any of the biologically acceptable polymers which are resistant may be used. Examples of such polymers are the polylactides, polyglycolides polydioxanone, polyolefins, polyesters, nylon and the like.

Figure 10:
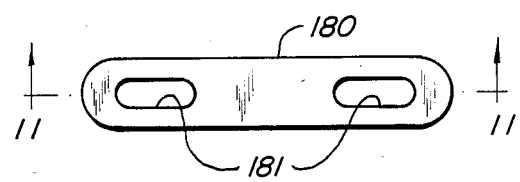
FIG. 10 is a plan view of one type of receiver according to the present invention.
Figure 11:
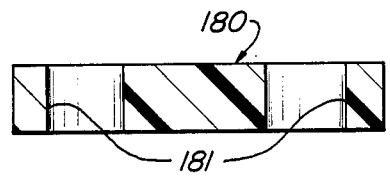
FIG. 11 is a cross-sectional view taken along line 11—11 of FIG. 10.

Another receiver which aids in insuring that the staple and receiver interlock is shown in FIGS. 10 and 11. In this embodiment, the receiver 180 has a pair of oval or elliptical openings 181. The long dimension of the opening is aligned the length of the receiver so that it will accept spreading of the legs of the staple. The smaller dimension of the opening is less than the diameter of the staple to interlock with the staple legs.

Another advantage of the rod or elliptical openings is that they reduce the amount of insertion force required for a given amount of interference fit. Reduced staple insertion force reduces the amount of manual force that the surgeon must provide during the stapling operation. The reduced insertion force also reduces or eliminates the need for closely controlled staple leg diameter and receiver hole dimensions.

Figure 13:
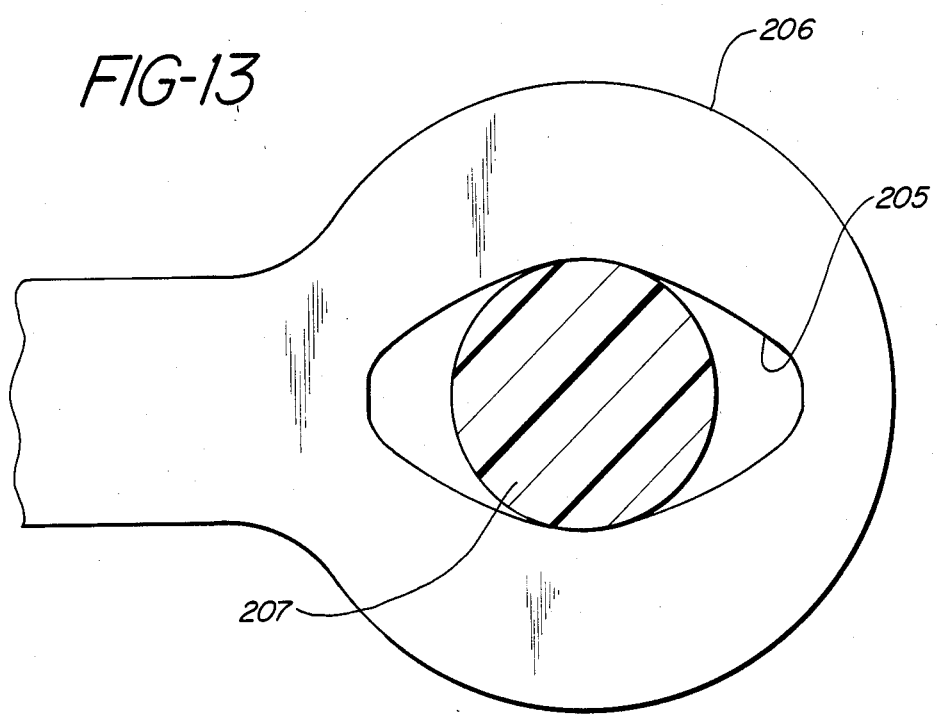
FIG. 13 is an enlarged plan view of one embodiment of a portion of a receiver of the present showing a staple leg in the receiver opening.

FIG. 13 shows a rectangular hole (205) receiver (206) deformed by a circular staple leg (207). The invention is not limited to elongated holes oriented along the major axis of the receiver. If desired, the elongated holes may be positioned with their major axis perpendicular to the major axis of the receiver. Also, the receiver holes may have shapes other than circular, oval or rectangular. The receiver holes may be triangular, square, polygonal of the like. Also, the staple legs may have cross-sections other than circular, such as triangular, oval, square and the like.

As may be appreciated the instruments of the present invention may be made from metals, plastics, woods, similar materials or various combinations thereof. If it is desired to make the instruments disposable, then the more inexpensive materials should be used. In most instances, it is desirable to make the instruments disposable because they are relatively complicated intricate mechanism which are difficult to resterilize.

The general operation of the instruments of the present invention is as follows. The tissues to be joined are placed between the stationary jaw and the movable jaw and are clamped in the space therebetween by moving the tissue locking member in the direction of the stationary jaw to interlock therewith. The tissue locking members aligns the jaws and once engaged allows the gap setting knob to be turned. On turning the gap setting knob the staple housing with the staples and the pusher and drive means is moved towards the stationary jaw. An appropriate gap generally corresponding to the thickness of the tissues to be joined is formed between the pair of jaws and is shown on the gauge. Thereafter, the interlock on the trigger mechanism is moved out of the way and the movable handle of the trigger mechanism actuated. This action forces the head of the pushed through the staple housing forcing the staples out of their holder through the tissue so that the legs pierce the tissue and engage the openings of the receivers held by the stationary jaw. Once the staple legs are engaged in the openings of the receivers, the friction holding means of the receivers is disengaged as well as the tissue locking member. After the joining operation has been completed, the gap between the jaws is opened by turning the gap control knob in the opposite direction.

It will be obvious to those skilled in the art that various modifications and changes may be made in the invention without departing from the spirit and scope thereof. The invention is not meant to be limited by that which is shown in the drawings and described in the specification. These changes and modifications are considered to fall within the scope of the present invention as defined by the appended claims.

What is claimed is:

1. A surgical instrument for joining tissue by means of two-piece fasteners, said fasteners comprising a staple and a receiver that interlocks with said staple, said instrument comprising:

a support body, a pair of jaws mounted at one end of said support body, a staple housing mounted in one of said jaws, said housing having a plurality of openings for accepting staples, staples disposed in said openings, each of said staples comprising a single piece of polymer, each staple comprising a pair of legs and a connecting portion connecting said legs whereby the staple has the general shape of an M, said connecting portion being resiliently compressible whereby when the legs are urged together by applying a force to the outside of each leg, the legs return to their original position upon removal of said force, said staples being held in said openings by forces applied to the outside of the staple legs by the walls of the openings, a plurality of receivers disposed in said other jaw, means mounted on said support body for moving said jaws containing said staple housing towards the other jaw to close the gap and clamp tissue placed therebetween, drive means mounted on said support body for driving the staples from the jaw on which the staple housing is mounted towards the opposite jaw to interlock with the receivers disposed in said opposite jaw, and actuating means mounted at the end of said support body opposite said end on which the jaws are mounted for actuating said staple drive means.

2. An instrument according to claim 1 wherein the legs of the M-shaped staple are parallel when the staple is disposed in the opening but said legs are not parallel when the staple is outside said opening.

3. An instrument according to claim 1 or 2 wherein the receivers include openings for engaging the legs of the staple and interlock therewith.

4. An instrument according to claim 3 wherein the openings in the receivers are tapered from a diameter larger than the diameter of the staple leg to a diameter somewhat smaller than the diameter of the staple leg.

5. An instrument according to claim 3 wherein the openings in the receiver are oval or elliptical in shape the smaller dimension of said oval or ellipse being less than the diameter of a staple leg to interlock therewith.

6. A two piece fastener for joining tissue, said fastener comprising a staple and a receiver that interlocks with the staple, said staple having the general shape of an M and comprising a pair of legs and a compressibly resilient connecting portion connecting said legs, each of said legs having a generally circular cross section, said receiver having a pair of openings for frictionally engaging the legs of said staple, said openings having an oval or elliptical shape with the smaller dimension of said opening being less than the diameter of the leg of the staple and the larger dimension of said opening being greater than the diameter of the leg of the staple.

7. A two piece fastener according to claim 6 wherein the legs of the staple are spread apart a distance greater than the distance between the openings in the receiver whereby when the staple legs are inserted in the receiver openings the distance between the legs is reduced and the legs are thereby retained by the receiver openings.

8. A two-piece fastener for joining tissue, said fastener comprising a staple and receiver that interlocks with the staple, said staple having the general shape of an M and comprising a pair of legs and a connecting portion connecting said legs, said connecting portion being compressibly resilient, said receiver having a pair of openings, said openings having a configuration different than the cross-sectional configuration of the staple legs whereby an interference fit is produced when the staple leg is inserted into an opening.

9. A two piece fastener for joining tissue said fastener comprising a staple and a receiver that interlocks with the staple, said staple comprising a pair of legs and a connecting portion connecting said legs, said staple having the general shape of an M and the connecting portion being resiliently compressible, said receiver having a pair of openings for frictionally engaging the legs of said staple, the distance between the legs of the staple being greater than the distance between the openings in the receiver whereby when the staple legs are inserted in the receiver opening the distance between the legs is reduced and the legs are thereby retained by the receiver openings.

10. A biologically acceptable two piece fastener comprising a staple and a receiver for joining human or animal tissue, said staple comprising a single piece of polymer, said staple having a pair of substantially parallel legs and a connecting portion connecting said legs whereby said staple has the general shape of an M, said connecting portion being resiliently compressible so that when the legs are urged together by applying a force to each leg, the legs return to their original position upon removal of said force whereby said staple may be held in an instrument for applying said staple by forces applied to the outside of the staple legs urging said legs towards one another, and a receiver for interlocking with said staple, said receiver having a pair of openings for frictionally engaging the legs of said staple, said openings having an oval or elliptical shape, with the smaller dimension of said opening being less than the diameter of the leg of the staple and the larger dimension of said opening being greater than the diameter of the leg of the staple.

* * * * *